(12) United States Patent
Zhou et al.

(10) Patent No.: US 11,964,249 B2
(45) Date of Patent: Apr. 23, 2024

(54) MILK PROTEIN CONCENTRATE-BASED MICROENCAPSULATION WALL MATERIAL AND MICROCAPSULES

(71) Applicant: Jiangnan University, Wuxi (CN)

(72) Inventors: Peng Zhou, Wuxi (CN); Jinhua Hu, Wuxi (CN); Fengchen Zhuang, Wuxi (CN); Xiang Li, Wuxi (CN); Yuejie Jin, Wuxi (CN); Chaoyue Zhang, Wuxi (CN); Minjun Cheng, Wuxi (CN); Yongxue Liang, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 436 days.

(21) Appl. No.: 17/123,415

(22) Filed: Dec. 16, 2020

(65) Prior Publication Data

US 2021/0101126 A1     Apr. 8, 2021

Related U.S. Application Data

(63) Continuation of application No. PCT/CN2018/095876, filed on Jul. 17, 2018.

(30) Foreign Application Priority Data

Jun. 27, 2018 (CN) .......................... 201810677817.0

(51) Int. Cl.
*B01J 13/04* (2006.01)
*A23J 3/08* (2006.01)
(Continued)

(52) U.S. Cl.
CPC ............ *B01J 13/04* (2013.01); *B01D 15/361* (2013.01); *B01F 23/4105* (2022.01); *B01F 23/804* (2022.01); *B01F 23/809* (2022.01); *A23J 3/08* (2013.01); *B01F 23/413* (2022.01); *B01F 23/4143* (2022.01)

(58) Field of Classification Search
None
See application file for complete search history.

(56) References Cited

FOREIGN PATENT DOCUMENTS

| CN | 101481404 A | 7/2009 |
| CN | 101816418 A | 9/2010 |

(Continued)

OTHER PUBLICATIONS

Liu. Dasong et al. Effect of Decalcification Pretreatment on the Solubility of Milk Protein Concentrate, Food and Fermentation Industries, vol. 43, No. 05, May 31, 2017 (May 31, 2017).

(Continued)

*Primary Examiner* — Jeffrey D Washville
(74) *Attorney, Agent, or Firm* — IPRO, PLLC

(57) ABSTRACT

The disclosure discloses a milk protein concentrate-based microencapsulation wall material and microcapsules, and belongs to the technical field of microcapsule preparation. In the disclosure, liquid or solid microcapsules are prepared by performing cation exchange treatment on milk protein concentrates, and then using the treated milk protein concentrates as a wall material. The prepared microcapsules have good physical and chemical stability during storage, and are suitable for protecting active functional factors and to be applied in the fields of food, medicine, health care products, cosmetics, daily chemicals and the like.

10 Claims, 18 Drawing Sheets

(51) Int. Cl.
   *B01D 15/36* (2006.01)
   *B01F 23/41* (2022.01)
   *B01F 23/80* (2022.01)

(56) References Cited

FOREIGN PATENT DOCUMENTS

| | | | |
|---|---|---|---|
| CN | 105685765 A | 6/2016 | |
| CN | 106417888 A | 2/2017 | |
| CN | 107095123 A | 8/2017 | |
| WO | 2006132553 A1 | 12/2006 | |
| WO | WO-2007110422 A2 * | 10/2007 | ............. A23C 21/00 |
| WO | WO-2016185053 A1 * | 11/2016 | ............. A23C 21/08 |
| WO | WO-2016207579 A1 * | 12/2016 | ........... A23C 9/1422 |

OTHER PUBLICATIONS

Hu,jinhua, et al. Effects of ion exchange decalcification on casein micelles, Food and Fermentation Industries,2016 vol. 42 No. 9. pp. 58-63.

Yang, Xiaojing et al. Effect of calcium-chelating salts on stability of formulated milk beverage during processing and storage, Journal of Diairy Science and Technology, Apr. 5, 2012, vol. 35 No. 3, pp. 4-8.

* cited by examiner

WPC

WPI+SC

MPC

MPC1

MPC2

MPC3

MPC4

MPC5

MILK PROTEIN CONCENTRATE-BASED MICROENCAPSULATION WALL MATERIAL AND MICROCAPSULES

TECHNICAL FIELD

The disclosure relates to a milk protein concentrate-based microencapsulation wall material and microcapsules, and belongs to the technical field of microcapsule preparation.

BACKGROUND

Milk protein concentrates (MPC) are high-protein milk powder made by removing most of lactose from skimmed milk by ultrafiltration, and have good functional properties and nutritional value. As far as the raw material itself is concerned, MPC has great application advantages. Compared with traditional milk protein ingredients, such as whey protein concentrates/isolates (WPC/WPI) and sodium caseinate (SC), the preparation process of MPC is simpler, can basically realize continuous and uninterrupted production, and has lower production costs and greener production methods. However, due to the limitation of membrane filtration technology, the emergence and development of MPC started relatively late, and its application research is still very limited.

In the preliminary research process, the inventor team explored the possibility of MPC application in the field of microcapsules. Microcapsules were prepared with unsaturated fatty acids as the core materials and MPC as the microencapsulation wall material. It was found that MPC as the microencapsulation wall material can protect the unsaturated fatty acids and delay their oxidation during storage. However, during the research process, it was also found that although MPC can be used as a microencapsulation wall material and microcapsule products can be prepared by technological measures such as spray drying or freeze drying, compared with products produced by the traditional milk protein microencapsulation high-quality wall material WPC or SC, the protective effect of the MPC as a wall material on the core material still has big defects. For example, when encapsulating polyunsaturated fatty acid conjugated linoleic acid (CLA), which is easily oxidized, WPC can provide an encapsulating rate of 90% or above, while MPC can only provide an encapsulating rate of about 80%. In a high temperature accelerated storage experiment, the oxidation rate of CLA encapsulated in MPC will be higher than that of WPC microcapsules, and the difference in the oxidation rate of some products will be about 7 times. These data all show that although MPC can be used to prepare microcapsule products, the encapsulating rate on the core material is very low; uneven shrinkage occurs during a spray drying process; the surface depression is deep; the inner wall is loose and has many cavities; the outer surface oil and capillary oil are high in content, and are easy to be oxidized in contact with air; and the microcapsule powder has poor dispersibility and solubility. That is, although natural MPC may be used as a microencapsulation wall material, it cannot be directly recommended for use as a microencapsulation wall material.

Therefore, to become a market-competitive product, the encapsulating rate of the MPC on the core material needs to be further improved, and the protection and improvement effects of the MPC on the physical and chemical stability of the core material need to be further improved too.

SUMMARY

To solve the above problems, the disclosure provides a microencapsulation wall material with high encapsulation efficiency and good core material protection effect, and a prepared microcapsule product. In the disclosure, MPC is pretreated, and the pretreated MPC is used as the microencapsulation wall material, wherein the pretreatment is performed by using ion exchange resin or adding exogenous reagents for acidity adjustment, ion chelation and the like.

The first objective of the disclosure is to provide a microencapsulation wall material suitable for preparing microcapsules. The microencapsulation wall material is pretreated MPC (milk protein concentrates); and the pretreatment is performed by using any of the following methods: ion exchange resin, addition of exogenous reagents for acidity adjustment and ion chelation, and the like.

In one implementation, the mass ratio of the ion exchange resin to the MPC (dry weight) to be treated is 1:30-3:1, optionally 2:3-4:3.

In one implementation, the condition of the ion exchange resin treatment is: 0.1-30 g of ion exchange resin is added to each 100 g of protein solution, and the mixed solution is stirred for a period of time for treatment.

In one implementation, the protein concentration of the protein solution is 1%-15%.

In one implementation, the added amount of the ion exchange resin is 0.1-30 g per 100 g of protein solution.

In one implementation, the ion exchange resin is preferably strongly acidic cation-exchange resin Amberlite SR1L Na.

In one implementation, the stirring in the ion exchange resin treatment is to stir at 500-5000 rpm for 0.5-6 h.

In one implementation, for the stirring in the ion exchange resin treatment, the preferred rotation speed is 1200-1500 rpm, and the preferred stirring time is 1-3 h.

In one implementation, the condition for adding the exogenous reagents for acidity adjustment is: a food-grade acidifier, such as hydrochloric acid, sulfuric acid, acetic acid, or glucolactone, is added to a protein solution to lower the pH of the protein, and then an ultrafiltration process is performed to obtain the pretreated MPC. The optimized treatment method is to lower the pH to around 5.6. The amount of each acid is different according to the properties. The key point of optimization is not to cause clogging of the system during the ultrafiltration process. The need for ultrafiltration to obtain the pretreated MPC results in the process complexity and cost increase point of the present implementation compared with ion exchange resin treatment.

In one implementation, the condition for adding the exogenous reagents for ion chelation is: a food-grade ion chelating agent, including EDTA, citric acid, malic acid and tartrate, is added to a protein solution. The optimized treatment method is to add a calcium ion chelating agent. Compared with the implementation of ion exchange resin treatment, the disadvantage of the present implementation is that the MPC solution pretreated by the exogenous reagent chelating ions contains more chelating agents.

In one implementation, the pretreatment is performed until the decalcification rate is 45% or above.

The second objective of the disclosure is to provide microcapsules, which use the pretreated MPC as the microencapsulation wall material. The pretreatment is performed using any of the following methods: ion exchange resin, addition of exogenous reagents for acidity adjustment or ion chelation, and the like.

In one implementation, the conditions of the ion exchange resin treatment are: 0-30 g ion exchange resin is added to 100 g protein solution, and the mixed solution is stirred at 500-5000 rpm for 0.5-6 h to obtain a series of different pretreated MPC protein solutions. The preferred ion exchange resin is strongly acidic cation-exchange resin Amberlite SR1L Na, the preferred added amount is 5-12 g of ion exchange resin per 100 g of protein solution, the preferred rotation speed is 1200-1500 rpm, and the preferred stirring time is 1-3 h.

In one implementation, the mass ratio of the ion exchange resin to the MPC (dry weight) to be treated is 1:30-3:1.

In one implementation, the microcapsules are liquid (that is, emulsions in various forms) or solid.

In one implementation, the emulsion may have many forms, including oil-in-water, as well as water-in-oil, water-in-oil-in-water, oil-in-water-in-oil, water-in-water-in-water and gelatinized internal water phase or external water phase or internal and external water phase.

In one implementation, the solid may be a microcapsule powder obtained by drying any of the above emulsions into a powder.

In one implementation, the preparation of the microcapsules is specifically as follows: after the pretreated MPC solution or a protein solution of a certain concentration prepared from the spray-dried powder of the pretreated MPC is accurately homogenized for 3 times at 10-50 MPa, the core material is added according to the ratio of core material to wall material=1:50-1:1 (w/w); after uniform stirring, dispersion is performed by a high-speed shearing disperser for 2 min; and then the mixture is homogenized for 2-6 times at a pressure of 10-50 MPa to obtain a uniform emulsion, that is, a kind of liquid microcapsules.

In one implementation, the microcapsules are solid; the preparation method comprises: the prepared emulsion is spray-dried immediately to prepare microcapsule powder, wherein the inlet temperature of spray-drying is 120-160° C., and by adjusting the flow of atomizing gas and the speed of a peristatic pump, the outlet temperature is controlled unchanged at 60-90° C.

The core material may be various environmentally sensitive active factors (such as vitamins, unsaturated fatty acids, probiotics and vaccines), volatile substances (such as essential oils), substances that need to change the gas or liquid existence form to the solid application form, etc.

In one implementation, the mass ratio of the pretreated MPC (dry weight) to the core material is 50:1-1:1.

In one implementation, the homogenization is performed at a pressure of 10-50 MPa for 2-6 times.

In one implementation, the inlet and outlet temperatures in spray-drying are respectively 120-160° C. and 60-90° C.

The third objective of the disclosure is to provide application of the microcapsules, which can be applied to the fields of food, medicine, health care products, cosmetics, daily chemicals, etc., to improve the physical and chemical stability of active functional factors, or change the application form to make the active functional factors easy to carry or redisperse.

The principle of the disclosure is to change the state of protein in the MPC and the interaction between the protein components through pretreatment, so that a continuous viscoelastic interface film can be formed when preparing the emulsion, and in the further drying process, a denser shell layer is formed to protect the core material.

Beneficial effects of the disclosure:

The disclosure improves the quality of microcapsule products prepared by using MPC as a wall material, improves the physical and chemical stability of the core material, and puts forward the application direction and fields of MPC, so that MPC can become a competitive milk protein ingredient, and can compete with traditional milk protein ingredients such as WPC and SC.

The disclosure effectively improves the encapsulation performance and protection performance of the milk protein concentrates as a microencapsulation wall material by pretreatment, increases the encapsulation rate of the core material from about 80% to 93% or above, and at the same time, by optimizing the density of the wall material, improves the oxidation stability of the core material, delays the deterioration of the core material, and better protects the activity of the core material.

The microcapsules of the disclosure are suitable for protecting active functional factors and to be applied to the fields of food, medicine, health care products, cosmetics, daily chemicals and the like.

DETAILED DESCRIPTION

Figure 1:
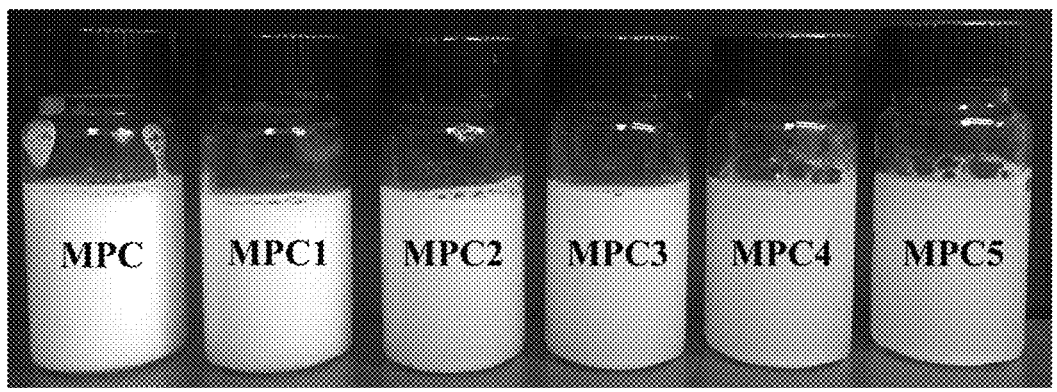
FIG. 1 Appearance images of MPC solutions with different decalcification rates.

Methods of index determination:

1. Determination of Microencapsulation Yield and Microencapsulation Efficiency

The test of total oil content in microcapsules mainly refers to the method of Kim et al.: 1 g of microcapsule powder is added in a 50 mL centrifuge tube, 8 mL of 50±5° C. deionized water is added, the mixture is mixed well until the sample is completely dispersed, and the mixture is put in running water to cool to room temperature. 40 mL of a mixed solvent of n-hexane/isopropanol (3:1, v/v) is added, and the mixture is mixed at room temperature for 20 min and then centrifuged (1500 g, 10 min). After the upper organic phase is collected, the lower water phase is extracted in the same way again. The organic phases are combined in a round-bottomed flask. After the organic solvent is removed by rotary evaporation, the round-bottomed flask is placed in an oven at 45° C. until the weight no longer changes. The total oil content in the microcapsules is calculated by the difference method.

Test of the surface oil content in microcapsules: 4 g of microcapsule powder is added to petroleum ether at 60° C., the mixture is slightly shaken and mixed for 10 min and then filtered, and the organic phase is collected in a round-bottomed flask. The round-bottomed flask is placed in a vacuum drying chamber at 45° C. until the weight no longer changes, and the surface oil content is calculated by the difference method.

Microencapsulation yield (%)=total oil content/addition amount of conjugated linoleic acid in formula×100%

Microencapsulation rate (%)=100%-surface oil content/total oil content×100%

2. Water Activity

The water activity of the microcapsule powder is tested by a LabSwift-aw water activity meter, and the instrument is calibrated with $a_w$=0.11 and $a_w$=0.23 standard solutions before the test. A proper amount of microcapsule powder (about 1 g) is taken in a test tank, and the value is read after the instrument is automatically balanced.

3. Test of Oxidation Stability of Conjugated Linoleic Acid (CLA) in Microcapsule Powder About 5 g of freshly prepared WPC-CLA, MPC-CLA and WPI+SC-CLA microcapsule powders are taken separately to fill 7.5 mL centrifuge tubes (not compacted, with no gap left at the top), and then the centrifuge tubes are sealed, wrapped with aluminum foil and stored in a thermostat at 35° C. for 45 days. The method is slightly changed during a storage experiment of the decalcified MPC-CLA microcapsule powder. About 5 g of powder is taken to fill a 7.5 mL centrifuge tube, compacted to remove air from the powder, and stored in a sealed dark place for 30 days.

The oxidation stability of the microcapsules is mainly evaluated by: (1) primary oxidation product-peroxide value (POV); (2) the content of hexanal, a representative oxidized volatile component of ω-6 series unsaturated fatty acids; and (3) the retention rate of conjugated linoleic acid.

4. Test of Peroxide Value (POV) of CLA in Microcapsule Powder

The disclosure mainly refers to Smet and GB/T 5009.37-2003 to test the peroxide value of CLA in the microcapsule powder. The specific operations are as follows:

0.25 g of the stored powder is taken in a 7.5 mL centrifuge tube, 4.75 mL of deionized water is added, and the mixture is mixed for 30 min to prepare a 5% (w/w) solution. 2 g of the solution is taken in a 15 mL centrifuge tube, 6 mL of chloroform-methanol mixed solution (2:1, v/v) is added, vortex is performed for 30 s, and the mixed solution is centrifuged at room temperature (12000 g, 20 min). 1 mL of the lower organic phase is taken in a 10 mL brown volumetric flask, 50 μL $FeCl_2$ (3.5 g/L) is added, and chloroform-methanol (7:3, v/v) is used to make the volume constant. 50 μL of KSCN solution (300 g/L) is added to the above solution, the mixed solution is placed for 5 min, and the absorbance is measured at 500 nm. The calculation of peroxide value refers to the national standard and is expressed as:

$$X=(C-C_0)\times V_1 \div (m\times V_2 \times 55.84 \times 2) \qquad (1)$$

Note: X-Peroxide value content (meq/kg) in the sample;

C—Mass of iron in the sample from a standard curve, in μg;

$C_0$—Iron mass of blank sample (pipe #0), in μg;

$V_1$—Total volume of the sample diluted, in millimeters (mL);

$V_2$—Sampling volume during determination, in millimeters (mL);

M—Total oil mass in the powder sample, in grams (g);

5. Test of Hexanal Content in Microencapsulated CLA

The hexanal content in microencapsulated CLA is tested using GC 2010 PLUS gas chromatography and a Turbo Matrix16 headspace sampler, and the specific operations are as follows:

0.5 g of microcapsule powder is taken in a 20 mL headspace bottle, and 3 mL of deionized water is added to dissolve the wall material. The headspace heating condition is 70° C., constant temperature for 30 min. The chromatographic column is an Rtx-Wax capillary column (30 m×0.25 mm, ID). The carrier gas is high-purity nitrogen, and the heating program is: after a constant temperature of 40° C. for 8 min, the temperature is increased to 230° C. at a rate of 10 K/min, and the temperature is kept constant for 7 min. The temperatures of the sampler and a detector are 180° C. and 250° C. respectively. Hexanal standard solutions of different concentrations are tested, and a standard curve is made to clarify the linear range. The hexanal content in the microencapsulated CLA is calculated based on the peak area, and expressed as mg/100 g CLA.

6. Test of Retention Rate of Microencapsulated CLA

In the present experiment, non-esterified conjugated linoleic acid in microcapsules is extracted and methylated by the method of Christie et al. The specific operations are as follows: first, 0.1 g of microcapsule powder is taken in 2 mL of deionized water, the mixture is mixed well, 8 mL of chloroform-methanol is added to the mixed solution (2:1, v/v), vortex is performed for 30 s, and the mixed solution is centrifuged (12000 g, 20 min). 2.5 mL of the centrifuged lower organic phase is sucked up using a syringe into a test tube. After blow-drying with nitrogen (37° C., 15 min), 1 mL of $BF_3$-methanol solution is added to react for 10 min for methyl esterification. After the methyl esterification is complete, 2 mL of n-hexane is added to extract the conjugated linoleic acid methyl ester in the water phase. The extracted n-hexane containing conjugated linoleic acid methyl ester is washed for 2 times with 5 mL of deionized water to remove the remaining methanol and other substances. After excess water is absorbed with anhydrous sodium sulfate, the conjugated linoleic acid is to be tested.

The content of conjugated linoleic acid is tested using GC2010 PLUS gas chromatography. The chromatographic column adopts DB-WAX capillary column (60 m×0.32 mm, ID), the carrier gas is high-purity nitrogen, and the heating program of the chromatographic column is: after a constant temperature of 160° C. is kept for 3 min, the temperature is increased to 220° C. at a rate of 2° C./min, and kept at 220° C. for 20 min. Standard solutions of conjugated linoleic acid methyl ester of different concentrations are prepared, and a standard curve is made. The content of conjugated linoleic acid in the storage sample is determined through the peak area ratio, and the retention rate of conjugated linoleic acid during storage is calculated.

To better explain the disclosure, the disclosure will be further explained in detail below in conjunction with specific examples.

EXAMPLE 1

Preparation of Conjugated Linoleic Acid Spray-Dried Microcapsule Powder 120 g of milk protein concentrate (MPC485) powder was accurately weighed and added in 880 g of deionized water to prepare a 12% protein solution. 0.02% of $NaN_3$ was added, and the mixed solution was stirred overnight and fully hydrated, and then homogenized 3 times under a pressure of 30 MPa. 0 g, 1.5 g, 3 g, 3.5 g, 8 g and 16 g of cation exchange resin Amberlite SR1L Na were added to every 100 g of protein solution respectively, and the mixed solutions were stirred at 1500 rpm for 2 h to obtain a series of different pretreated MPC protein solutions (with the numbers of MPC0, MPC1, MPC2, MPC3, MPC4 and MPC5, and the determined decalcification rates of 0%, 14.0%, 27.6%, 28.0%, 45.2% and 59.2% respectively) for use.

Different proteins are accurately weighed and prepared into protein solutions with a mass concentration of 12%. Specifically, 120 g WPC (whey protein concentrates), MPC, WPI+SC (whey protein isolates WPI and sodium caseinate SC, the mixing ratio of the two proteins is 1:4, w/w), and pretreated MPC powders (MPC0, MPC1, MPC2, MPC3, MPC4 and MPC5) with the decalcification rates of 0%, 14.0%, 27.6%, 28.0%, 45.2% and 59.2% were weighed and added to deionized water respectively to prepare 12% protein solutions. 0.02% of $NaN_3$ was added respectively, and the mixed solutions were stirred overnight and fully hydrated, and then homogenized 3 times under a pressure of 30 MPa for use.

The above solutions with a protein concentration of 12% were used as wall materials and added to conjugated linoleic acid (CLA) at the ratio of core material to wall material=1:8 (w/w). After uniform stirring, dispersion was performed by a high-speed shearing disperser for 2 min. The mixture was homogenized 3 times under a pressure of 30 MPa to obtain a uniform emulsion.

The prepared emulsion is spray-dried immediately, wherein the inlet temperature of spray-drying is 160° C., and by adjusting the flow of atomizing gas and the speed of a peristaltic pump, the outlet temperature is controlled unchanged at 80° C. The flow rate of the atomizing gas and the flow rate of the peristaltic pump were about 414 L/h and 13.3 mL/min, respectively. The freshly prepared microcapsules were collected in a waterproof aluminum foil bag, and stored in an ultra-low temperature refrigerator at −70° C. The samples were balanced in a silica gel drier for 2 h before use.

Figure 2:
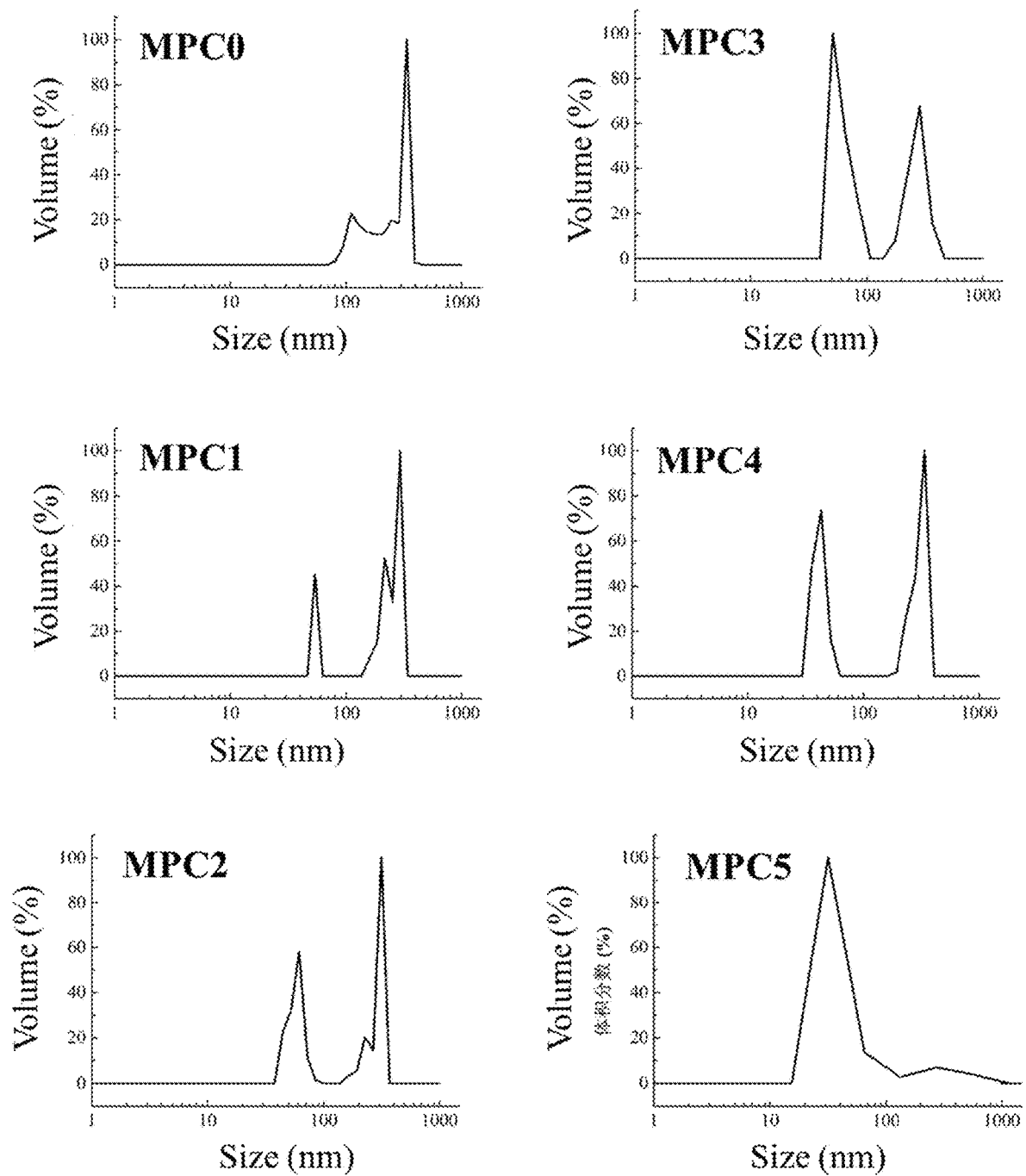
FIG. 2 Particle size distribution of MPC solutions with different decalcification rates.
Figure 3A:
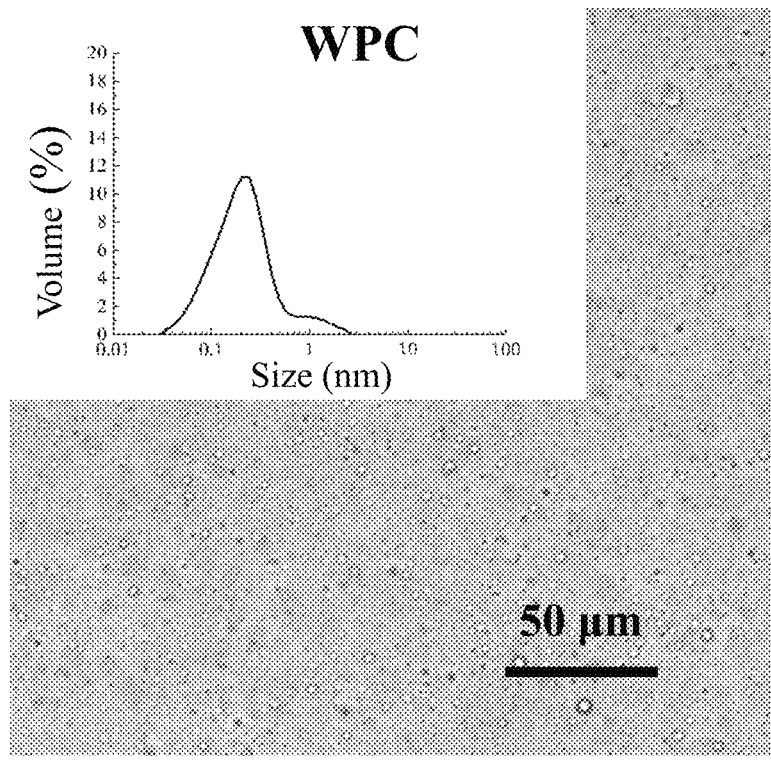
FIG. 3A Particle size distribution and optical microscope image of milk protein-conjugated linoleic acid (CLA of WPC) emulsion.
Figure 3B:
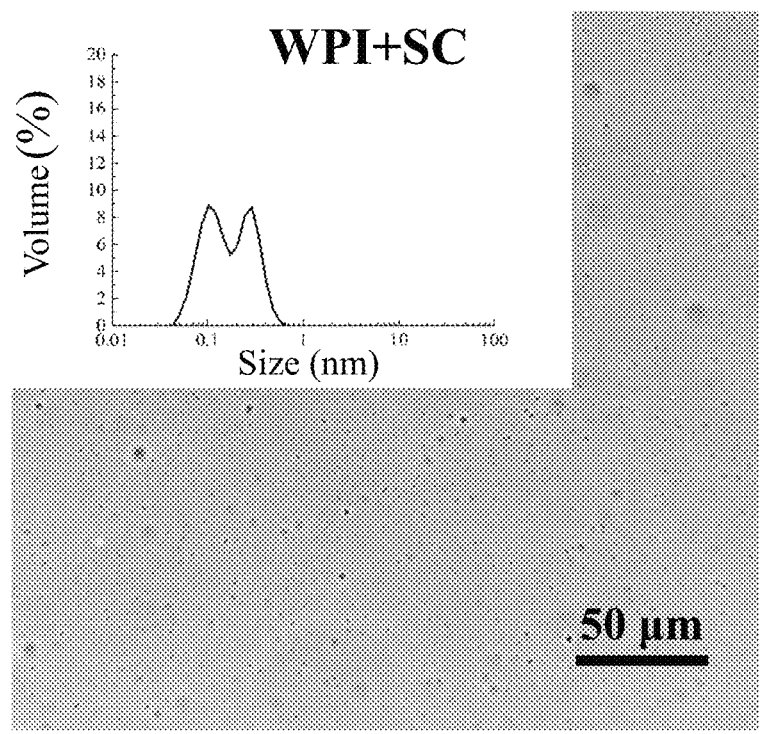
FIG. 3B Particle size distribution and optical microscope image of milk protein-conjugated linoleic acid (CLA of WPI+SC) emulsion.
Figure 3C:
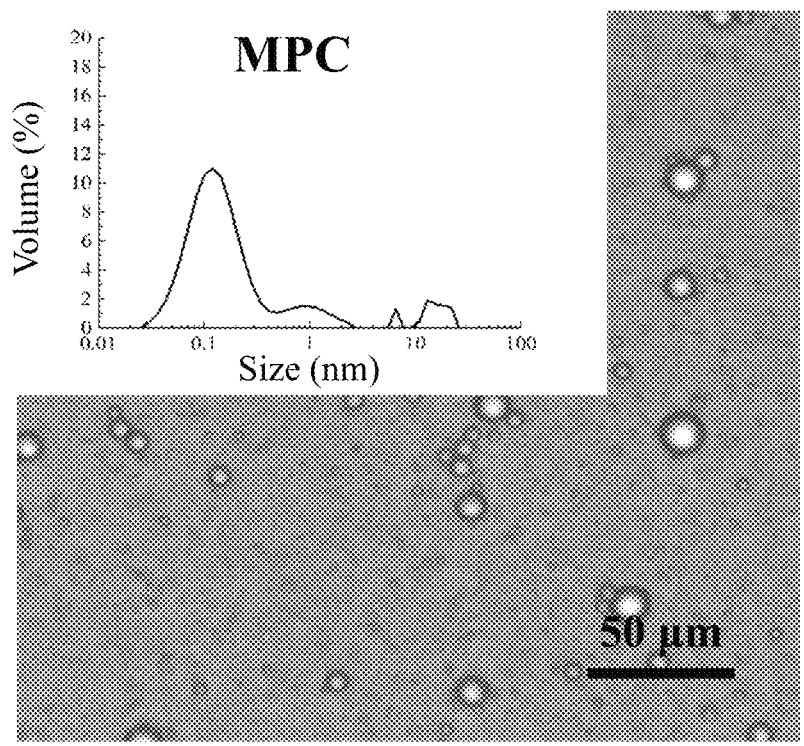
FIG. 3C Particle size distribution and optical microscope image of milk protein-conjugated linoleic acid (CLA of MPC) emulsion.
Figure 3D:
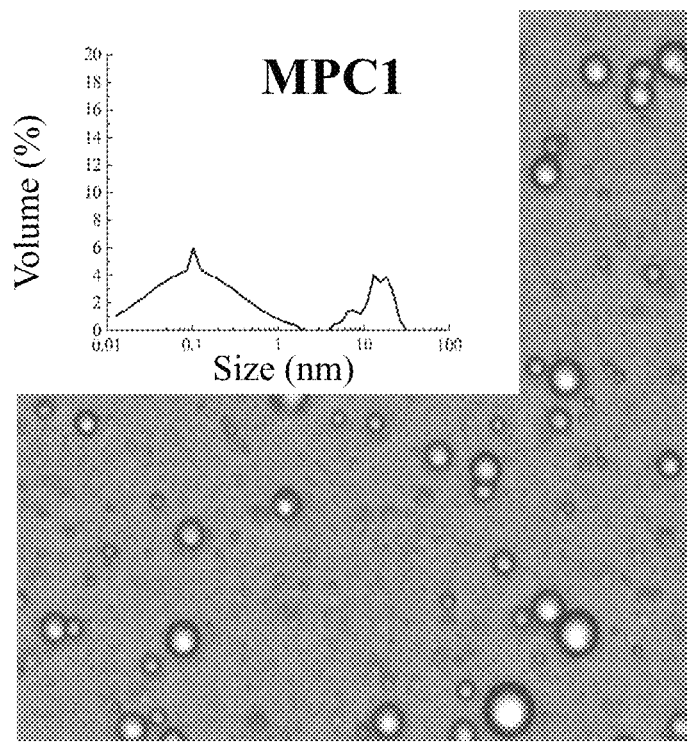
FIG. 3D Particle size distribution and optical microscope image of milk protein-conjugated linoleic acid (CLA of MPC1) emulsion.
Figure 3E:
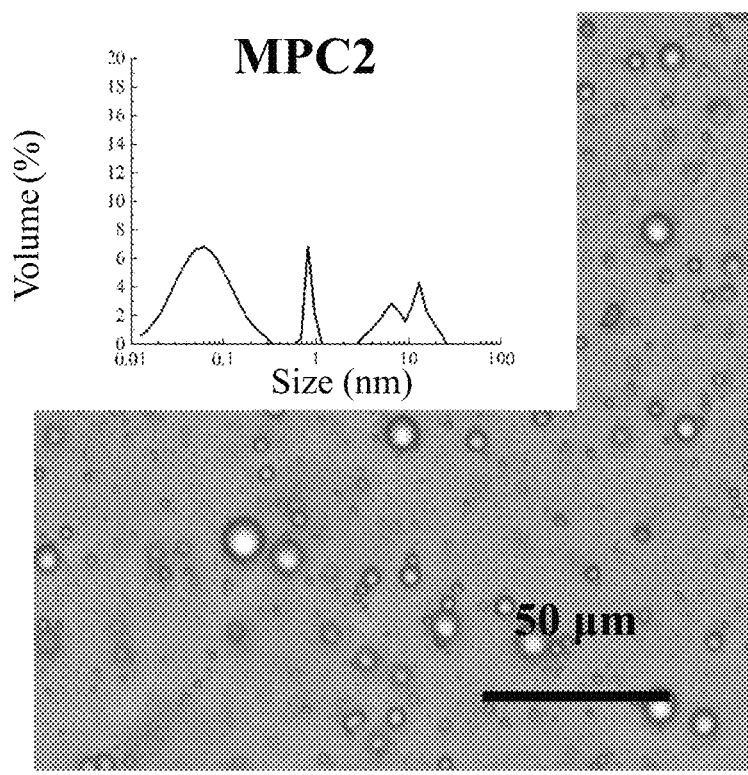
FIG. 3E Particle size distribution and optical microscope image of milk protein-conjugated linoleic acid (CLA of MPC2) emulsion.
Figure 3F:
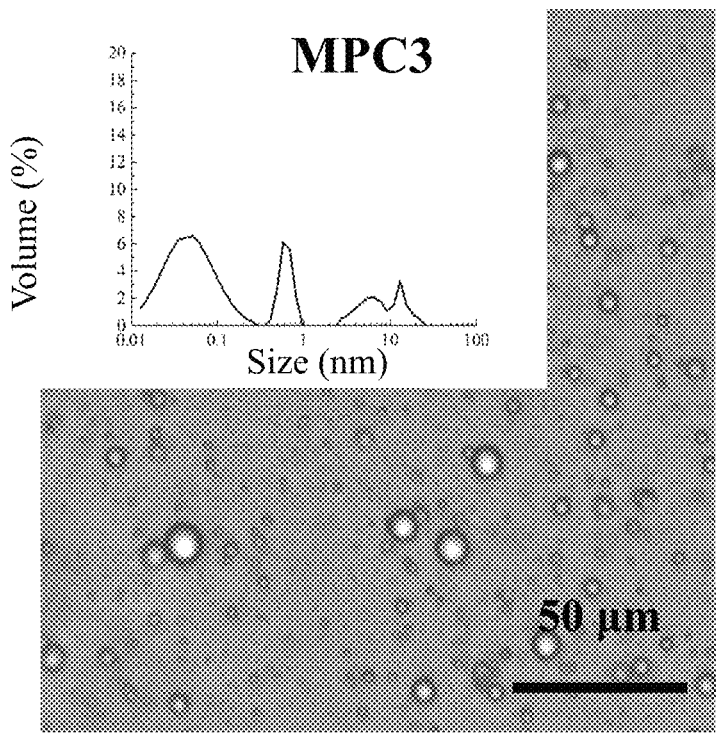
FIG. 3F Particle size distribution and optical microscope image of milk protein-conjugated linoleic acid (CLA of MPC3) emulsion.
Figure 3G:
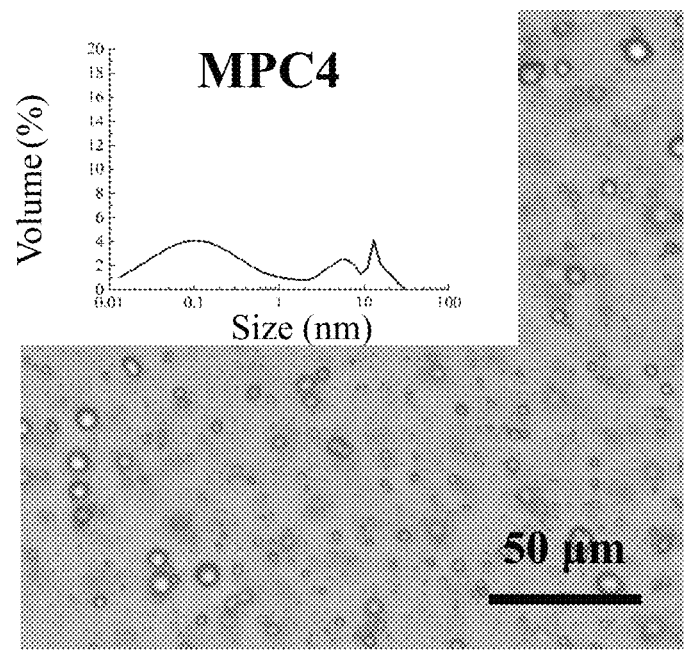
FIG. 3G Particle size distribution and optical microscope image of milk protein-conjugated linoleic acid (CLA of MPC4) emulsion.
Figure 3H:
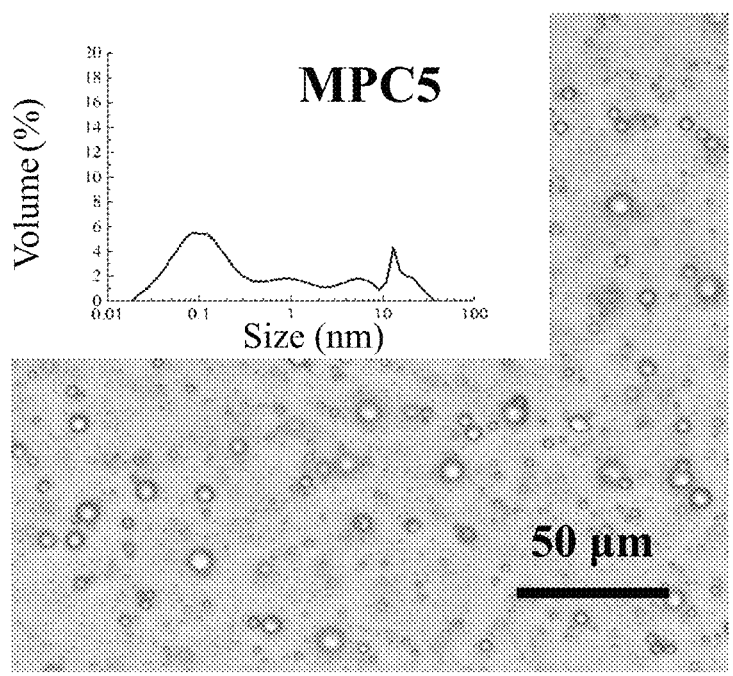
FIG. 3H Particle size distribution and optical microscope image of milk protein-conjugated linoleic acid (CLA of MPC5) emulsion.
Figure 4:
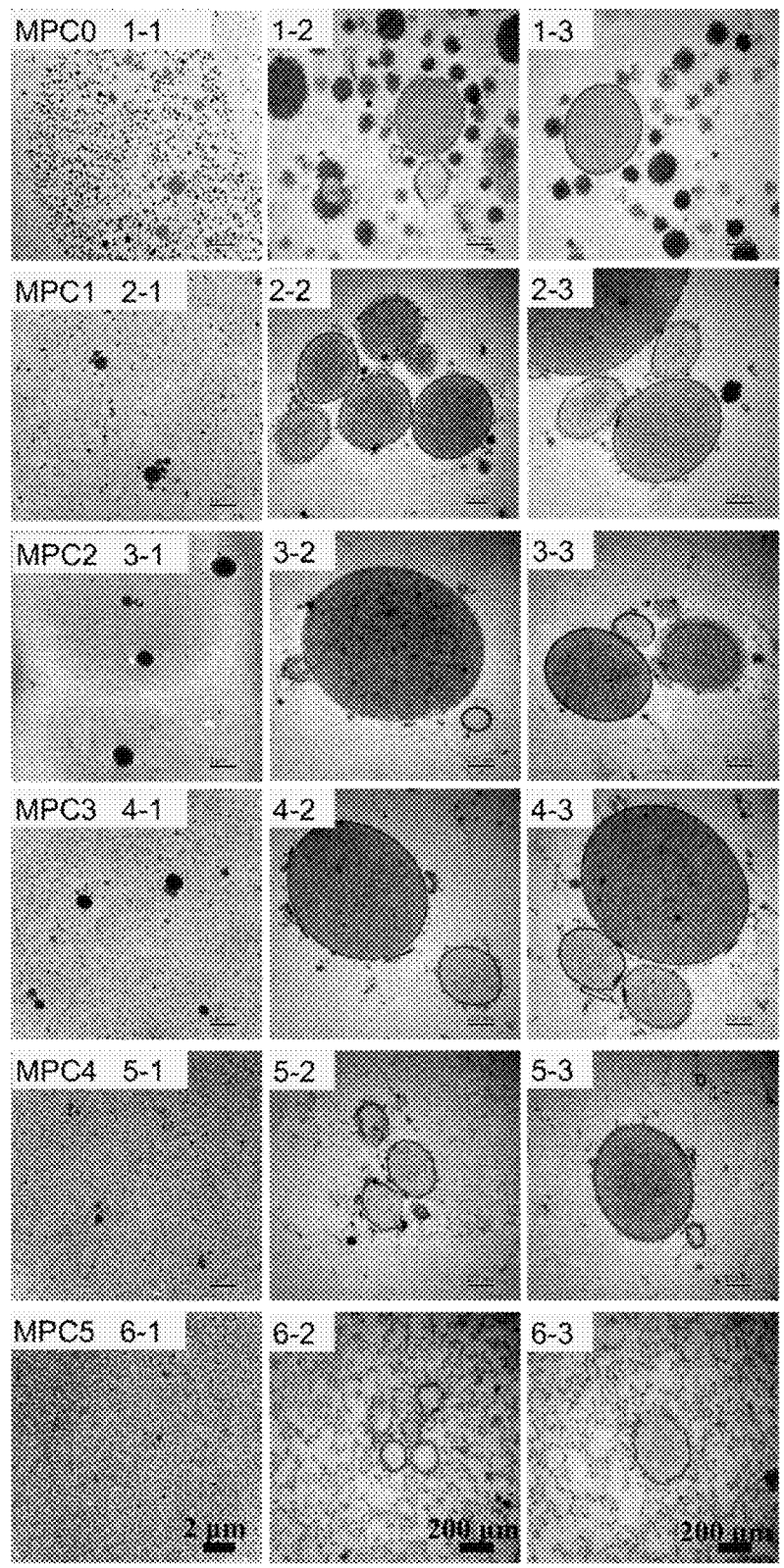
FIG. 4 Transmission electron microscope image of milk protein-conjugated linoleic acid (CLA) emulsion, protein magnification: 1-5k times; 2-50k times; 3-50k times.
Figure 5A:
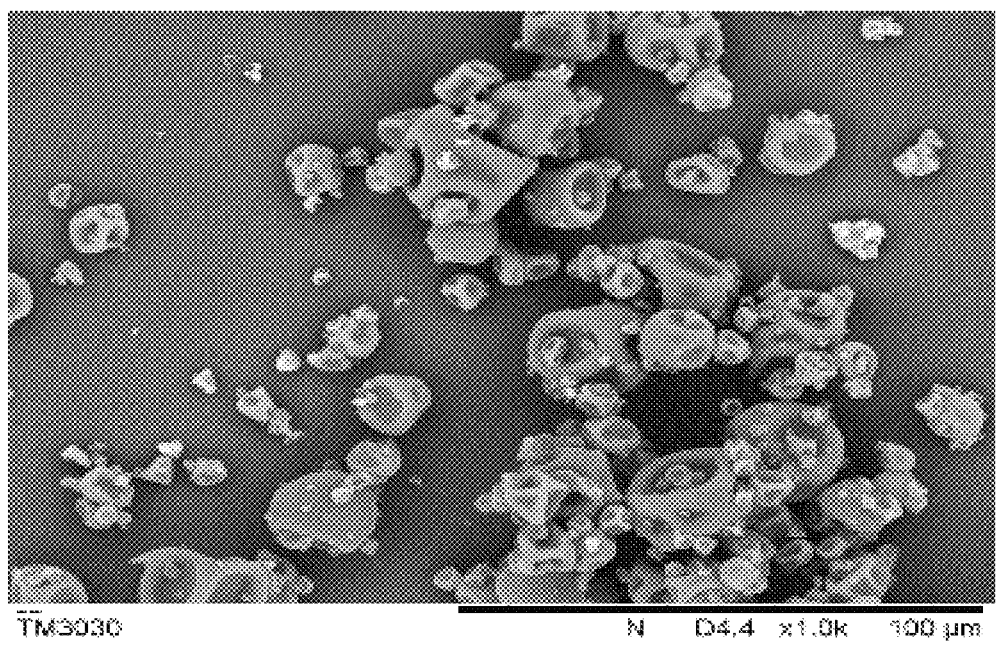
FIG. 5A Scanning electron microscope image I of milk protein-conjugated linoleic acid (CLA of WPC) microcapsule powder.
Figure 5A:
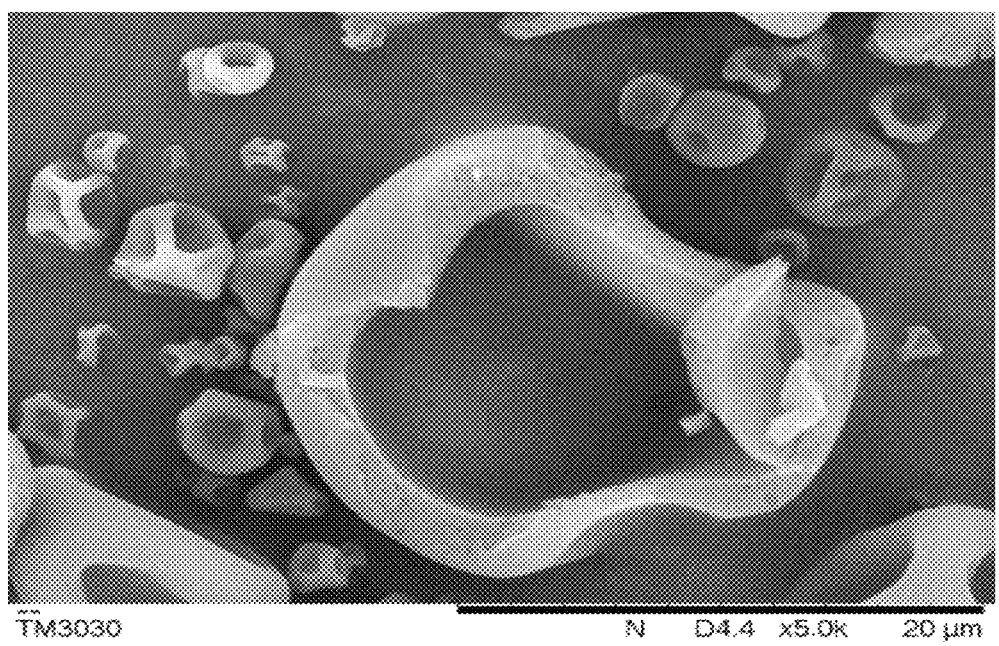
Figure 5B:
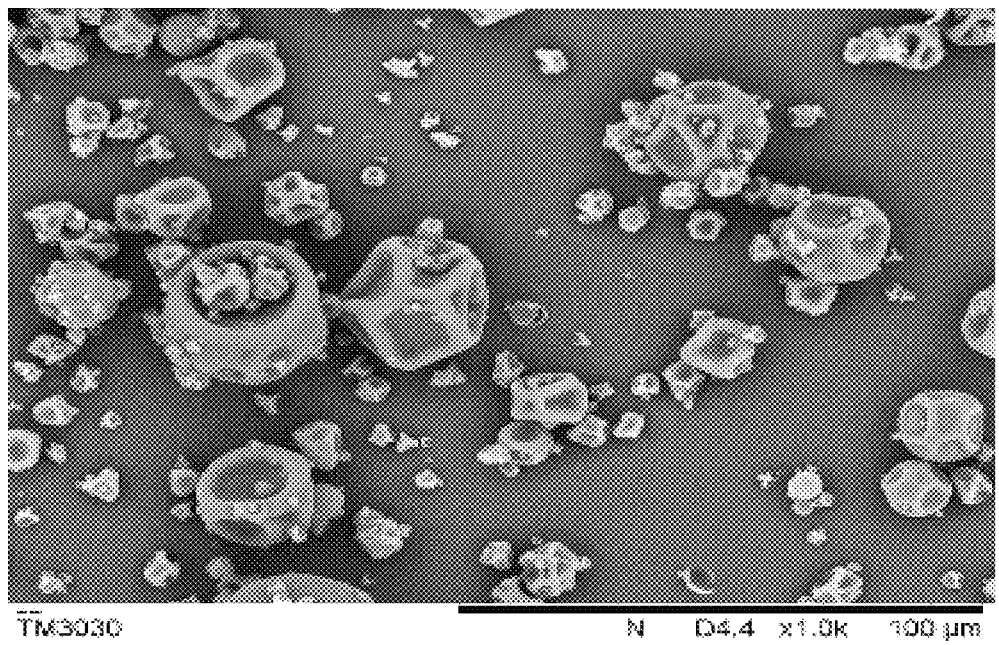
FIG. 5B Scanning electron microscope image I of milk protein-conjugated linoleic acid (CLA of WPI+SC) microcapsule powder.
Figure 5B:
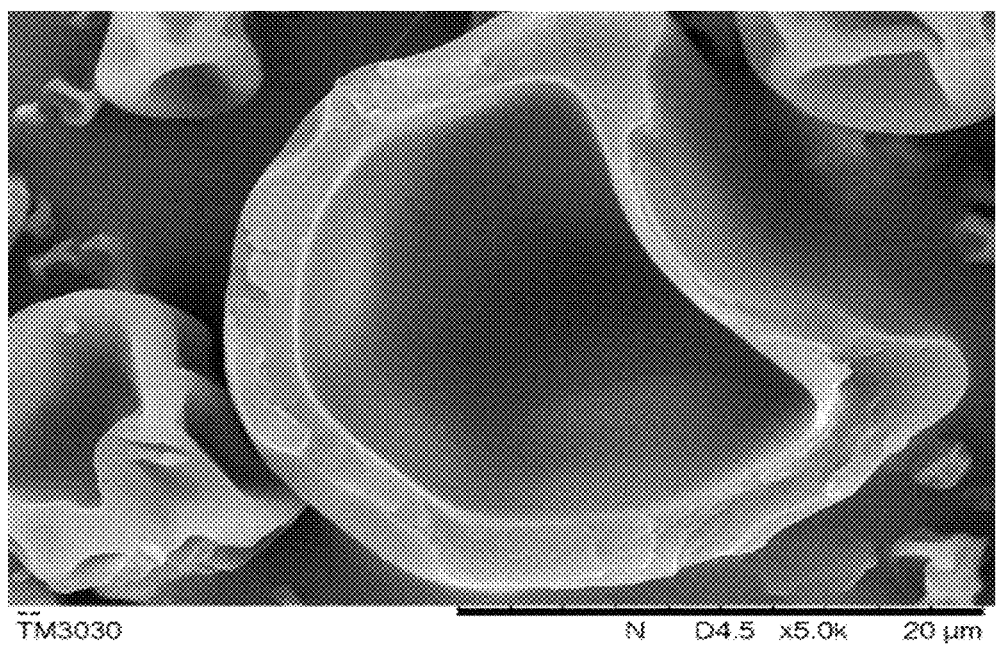
Figure 5C:
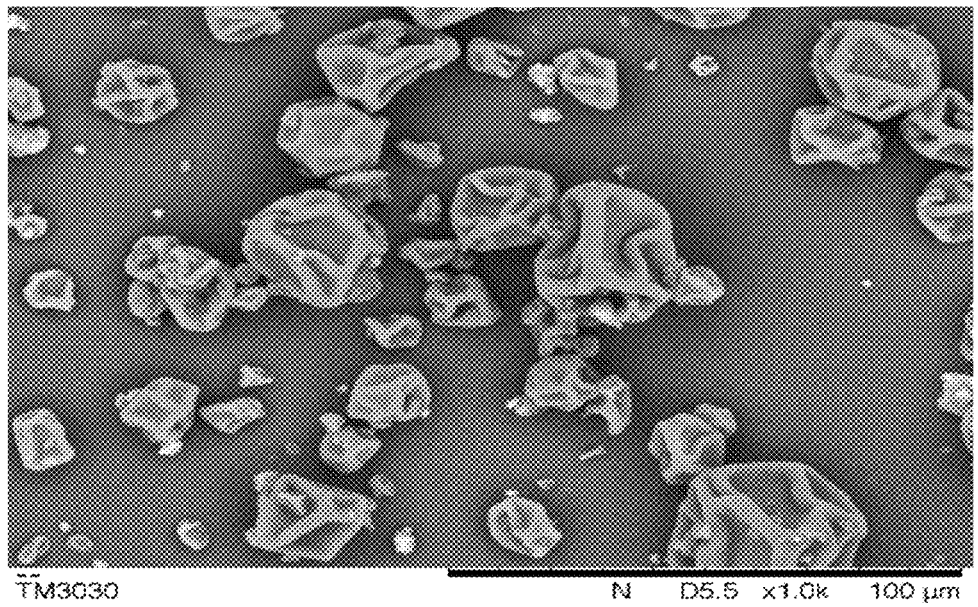
FIG. 5C Scanning electron microscope image I of milk protein-conjugated linoleic acid (CLA of MPC) microcapsule powder.
Figure 5C:
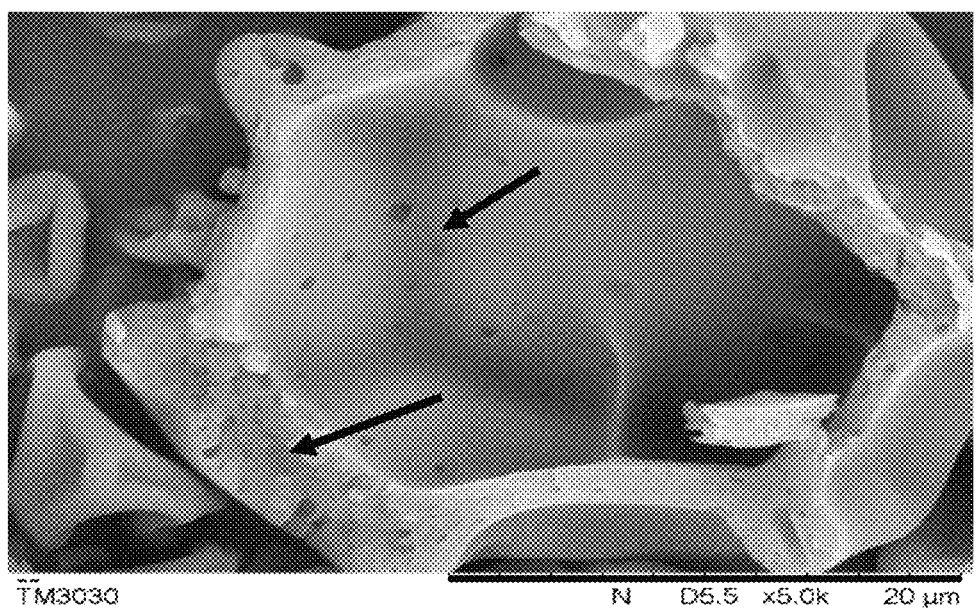
Figure 5D:
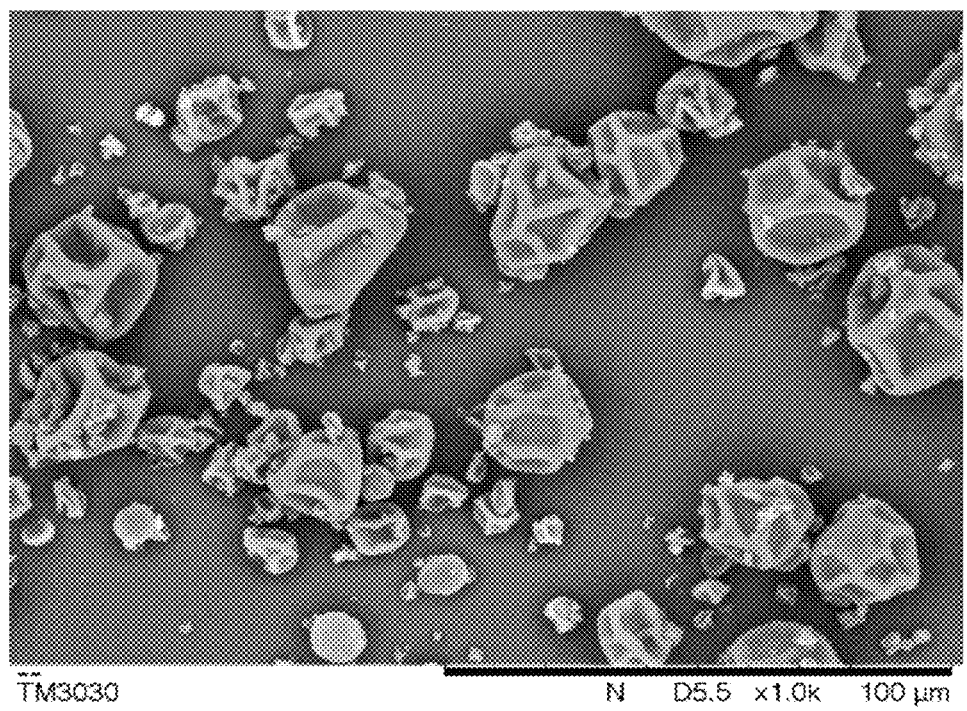
FIG. 5D Scanning electron microscope image I of milk protein-conjugated linoleic acid (CLA of MPC1) microcapsule powder.
Figure 5D:
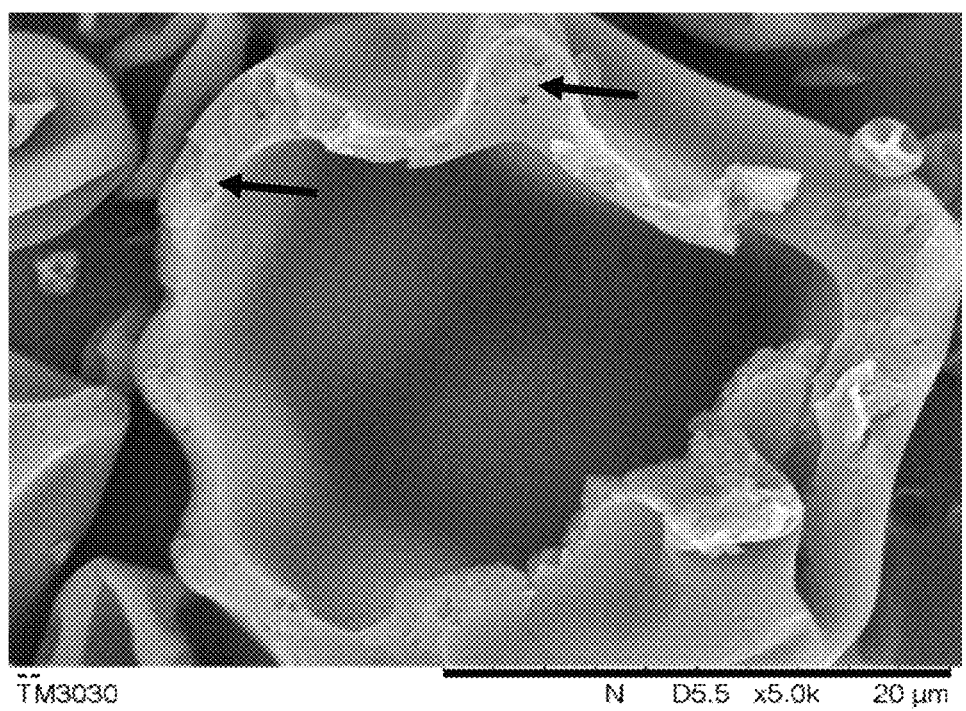
Figure 6A:
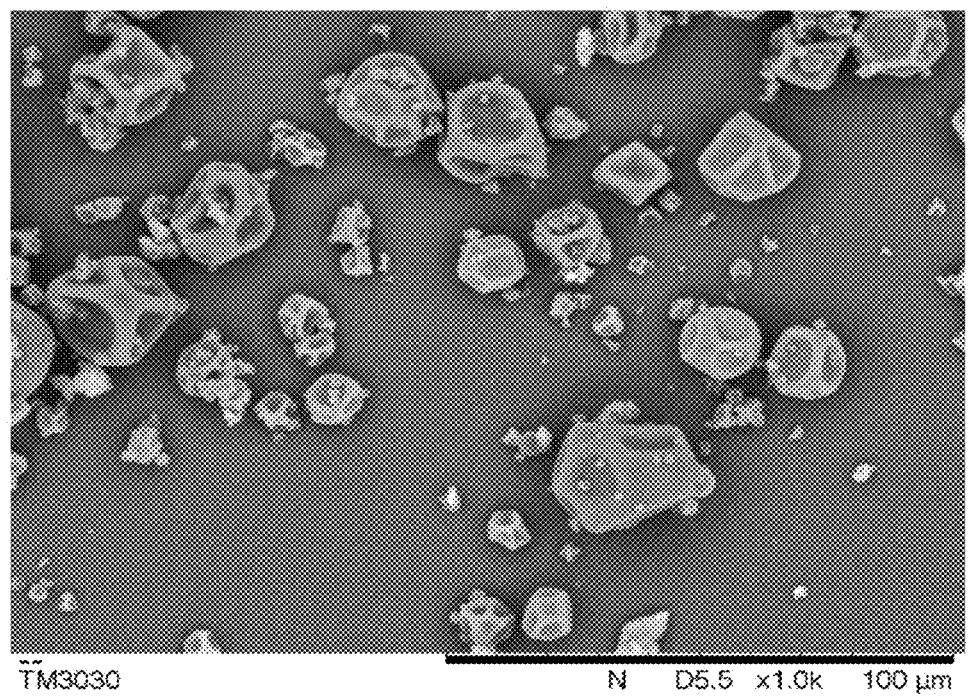
FIG. 6A Scanning electron microscope image II of milk protein-conjugated linoleic acid (CLA of MPC2) microcapsule powder.
Figure 6A:
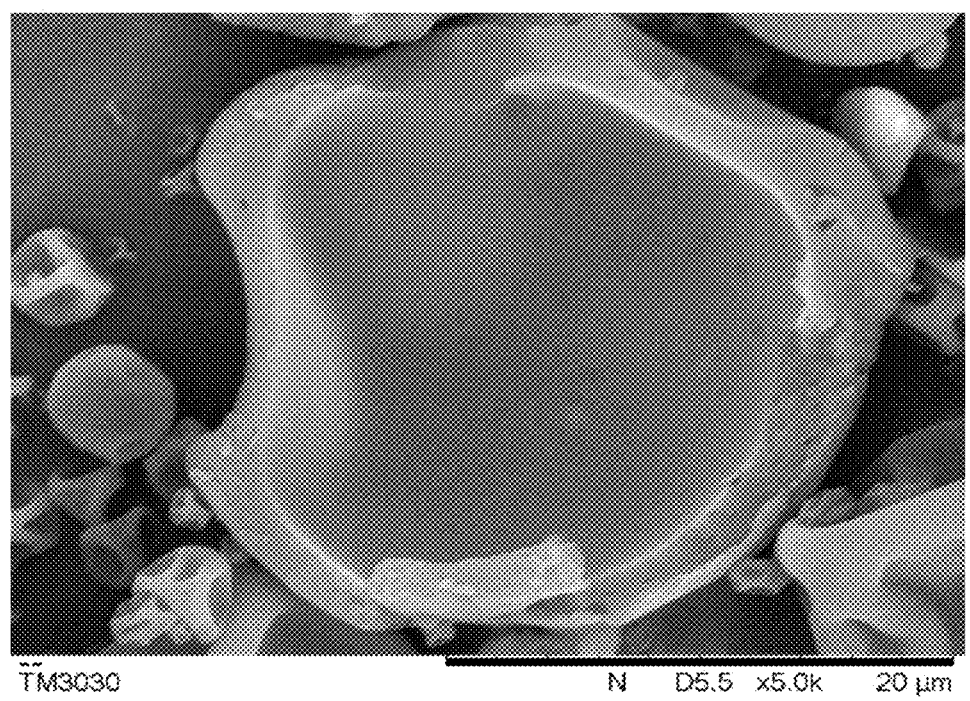
Figure 6B:
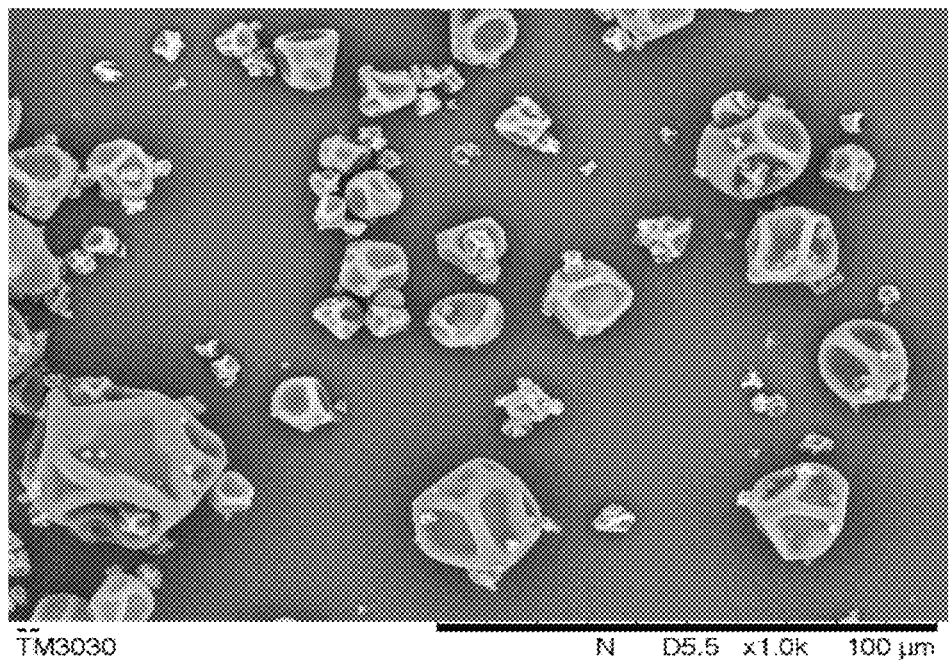
FIG. 6B Scanning electron microscope image II of milk protein-conjugated linoleic acid (CLA of MPC3) microcapsule powder.
Figure 6B:
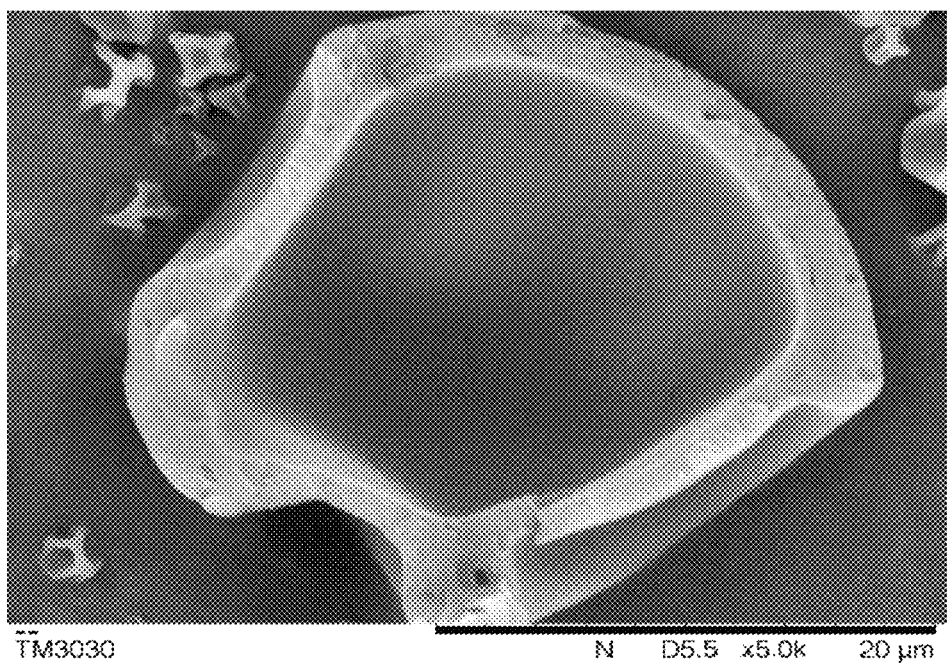
Figure 6C:
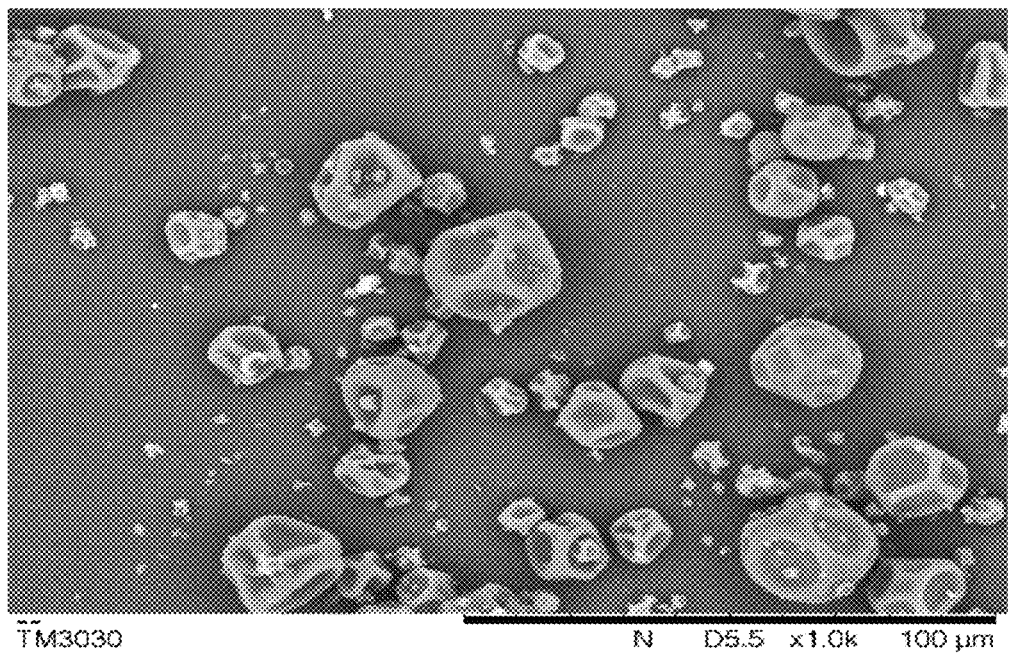
FIG. 6C Scanning electron microscope image II of milk protein-conjugated linoleic acid (CLA of MPC4) microcapsule powder.
Figure 6C:
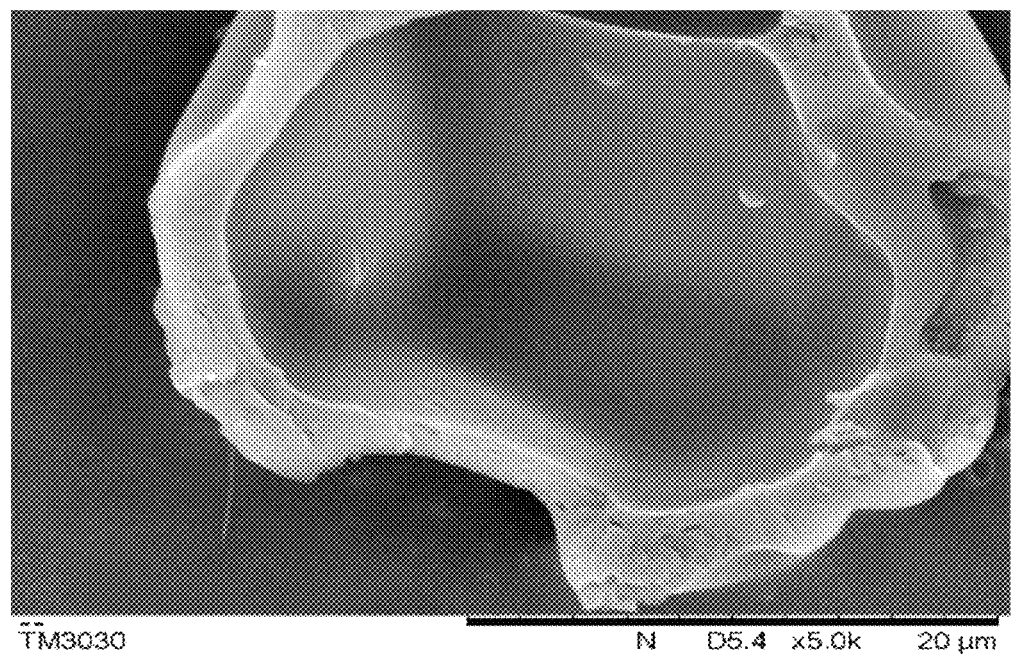
Figure 6D:
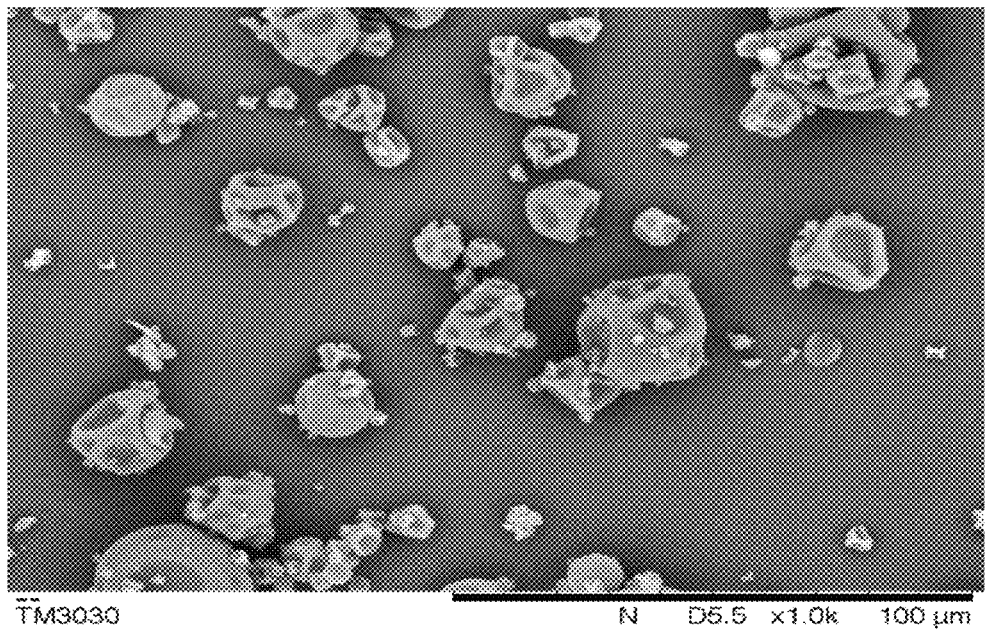
FIG. 6D Scanning electron microscope image II of milk protein-conjugated linoleic acid (CLA of MPC5) microcapsule powder.
Figure 6D:
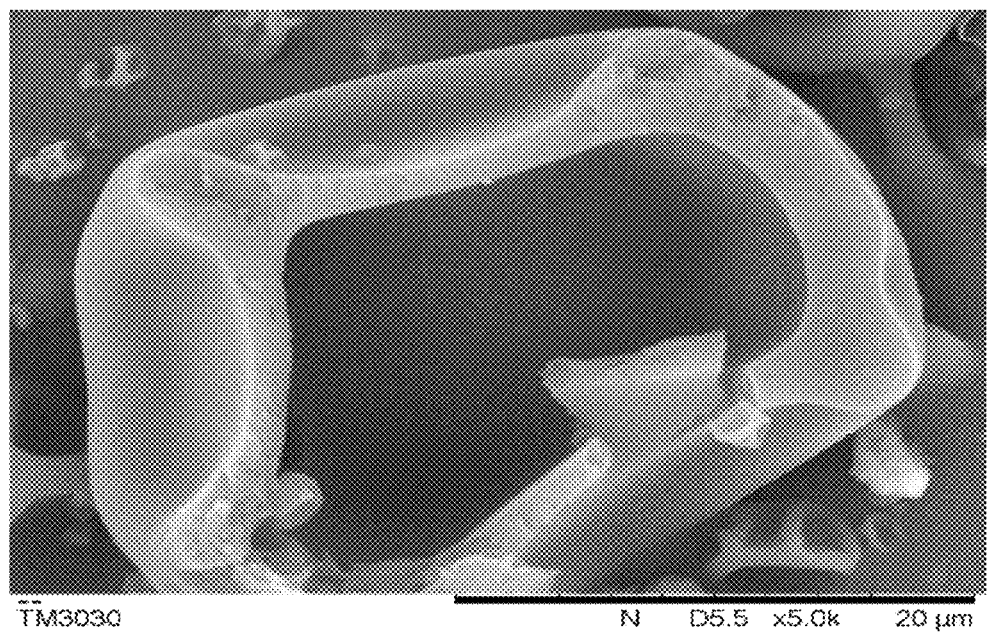
Figure 7A:
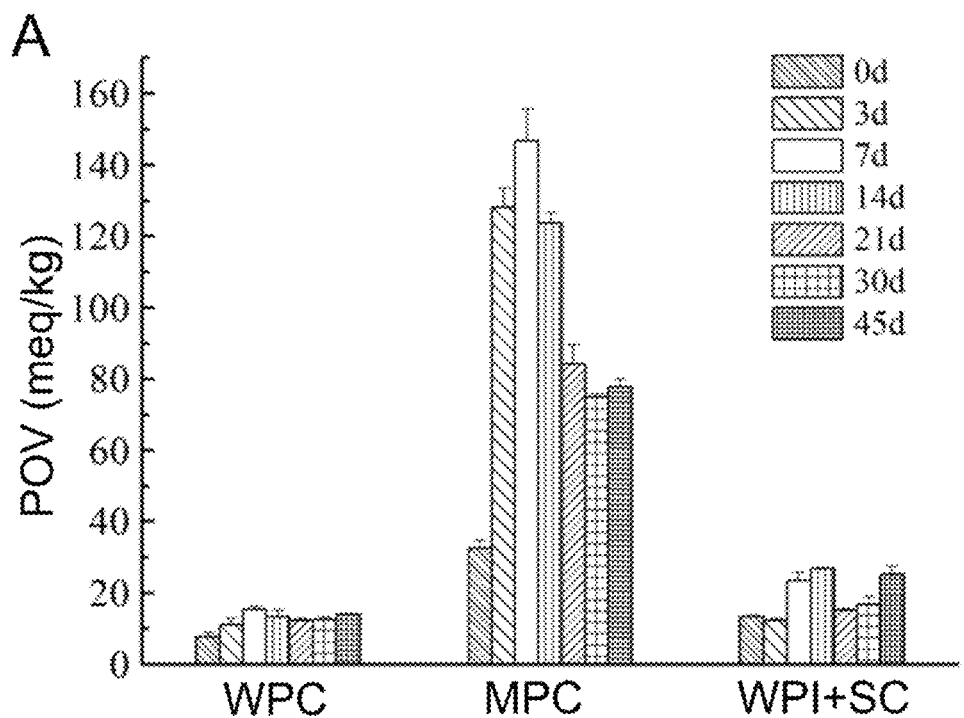
FIG. 7A Changes in peroxide value (POV) of CLA (WPC,MPC,WPI+SC)in microcapsule powder during storage.
Figure 7B:
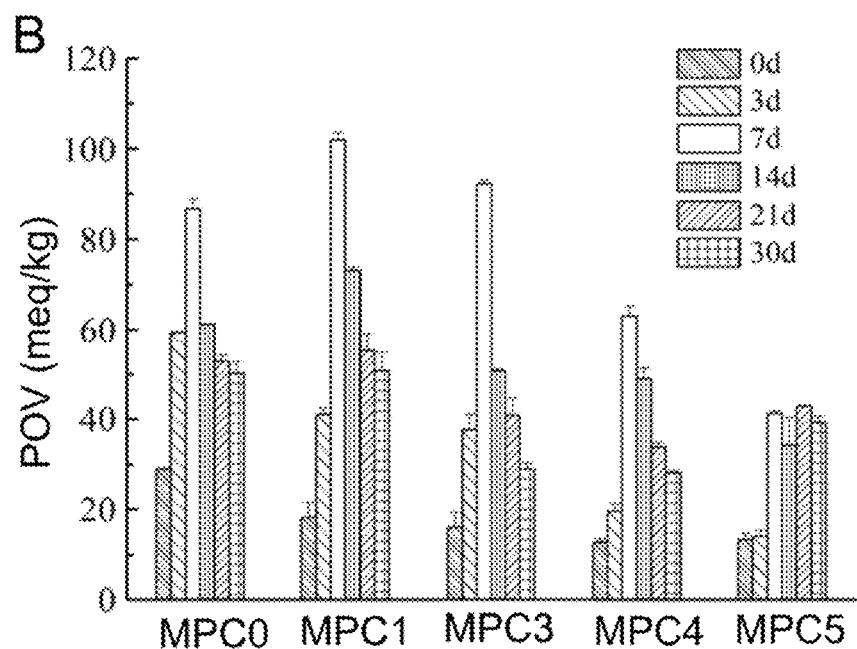
FIG. 7B Changes in peroxide value (POV) of CLA (MPC0, MPC1, MPC3,MPC4, MPC5)in microcapsule powder during storage.
Figure 8A:
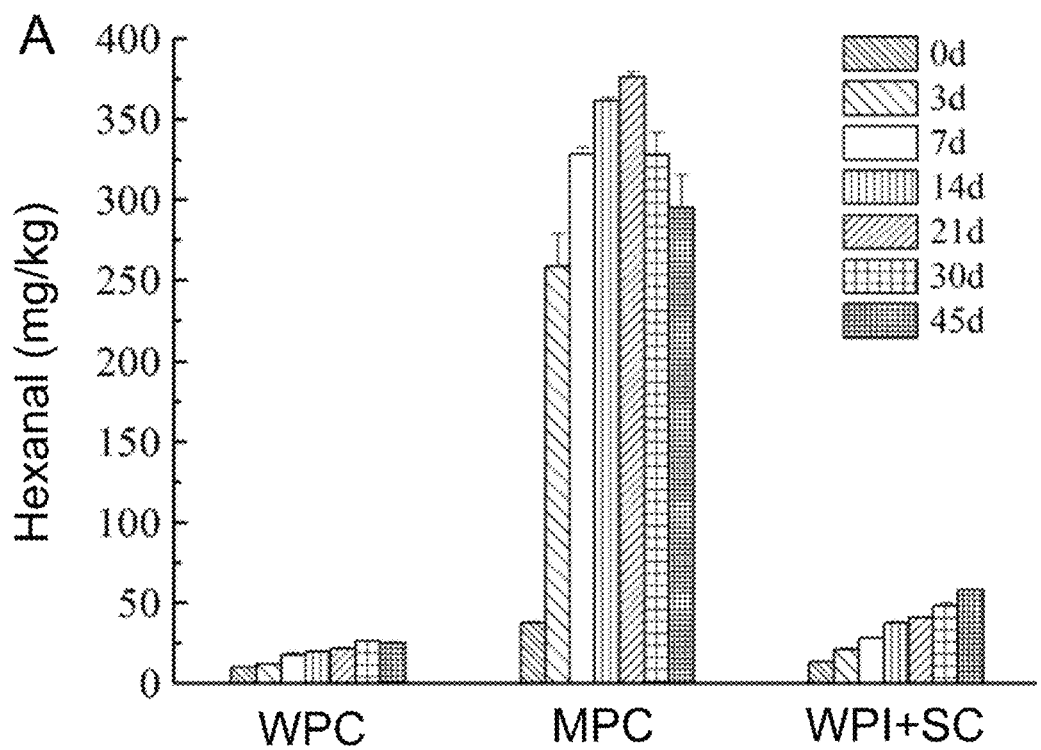
FIG. 8A Changes in hexanal content of microencapsulated CLA (WPC,MPC,WPI+SC)during storage.
Figure 8B:
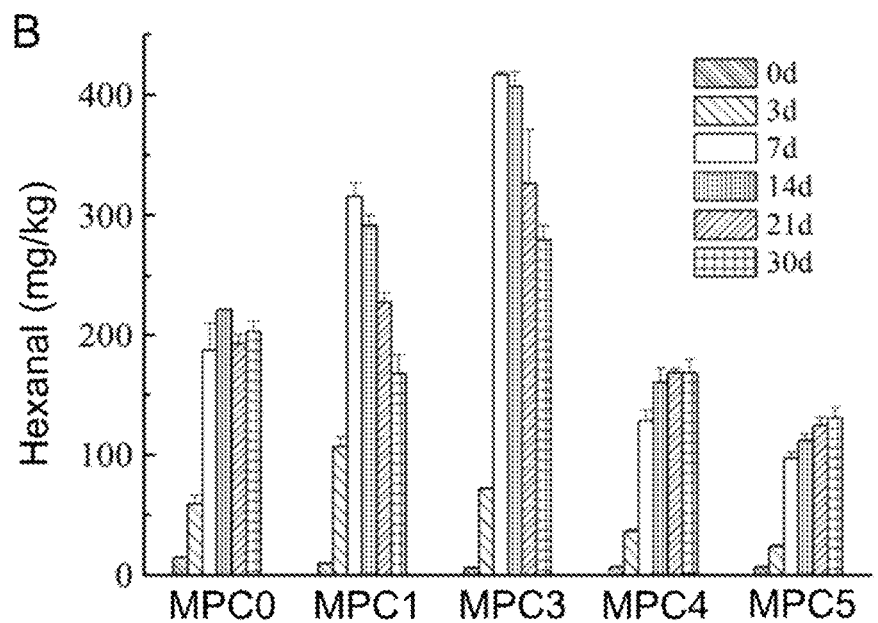
FIG. 8B Changes in hexanal content of microencapsulated CLA (MPC0, MPC1, MPC3, MPC4, MPC5)during storage.

The appearance of the solutions (FIG. 1) and particle size distribution (FIG. 2) of the treated MPC are shown. Removal of calcium ions in the MPC solution will dissociate the colloidal calcium phosphate in the casein micelles, and the change of the colloidal calcium phosphate, which is the backbone of the micelles, will inevitably cause changes in the structure of the casein micelles. The appearance characteristics of the MPC solutions with different degrees of decalcification were described by taking pictures. FIG. 1 shows that when the decalcification rate increases from 0% to 28.0%, the MPC solutions gradually change from milky white to light yellow; and when the decalcification rate continues to rise to 59.2%, the MPC wall material solution is relatively clear, transparent and slightly yellow. The appearance pictures of the protein solutions preliminarily indicate that the higher the decalcification rate, the less micellar structure in MPC. The change of turbidity in the appearance of the decalcified MPC solutions preliminarily indicates the dissociation of the micellar structure in the solution. On the basis, the particle size and distribution of the decalcified MPC solution were tested, as shown in FIG. 2. When the decalcification rate is 0%, the particle size distribution of the protein in the MPC solution is mainly 80-450 nm. When the decalcification rate is 14.0%, the particle size distribution diagram of the decalcified MPC wall material solution has a new small peak around 45 nm, indicating that the micelles in MPC dissociate on a small scale at the time, and generate a part of casein micelle fragments. With further increase of the decalcification rate, the volume ratio of the small peak in the particle size distribution diagram of the decalcified MPC solution becomes larger and larger, indicating that the micelles further dissociate. When the decalcification rate is 59.2%, the particle size distribution of the MPC solution is mainly 20-100 nm, that is, most of the micelles have dissociated.

Optical microscope images and particle size distribution of different milk protein-conjugated linoleic acid emulsions, transmission electron microscope images of the emulsions, scanning electron microscope images of microcapsule powder obtained by spray-drying, as well as changes in the peroxide value (POV), change in the hexanal content, change in the CLA retention rate and the like of CLA in the microcapsule powder in the storage process were analyzed, and the results are shown in FIG. 1 to FIG. 9.

Take the traditional milk protein wall materials of WPC (whey protein concentrates), and WPI (whey protein isolates)+SC (sodium caseinate) (without micellar structure) as a reference, the microencapsulation efficiency of untreated MPC is relatively low, and the microencapsulation efficiency of MPC-CLA prepared from treated MPC is improved to be comparable to that of traditional wall materials (Table 1). The particle size and distribution of the emulsion (FIG. 3A-FIG. 3H), the morphology of the emulsion (FIG. 4), and the morphology and internal structure of the microcapsule powder (FIG. 5A-FIG. 5D and FIG. 6A-FIG. 6D) show that: the presence of the casein micelle structure in MPC will increase the particle size of oil droplets in the emulsion, the corresponding microencapsulation efficiency decreases, oil distribution in the microcapsules is uneven, the surface of the powder has deep depressions, and there are many cracks and holes in the inner wall.

TABLE 1

|  | Microencapsulation efficiency (%) | Water activity |
|---|---|---|
| WPC | 96.3 ± 1.0 | 0.209 ± 0.003 |
| WPI + SC | 95.6 ± 0.3 | 0.229 ± 0.005 |
| MPC0 | 84.4 ± 0.5 | 0.237 ± 0.006 |
| MPC1 | 92.1 ± 1.4 | 0.235 ± 0.002 |
| MPC2 | 91.6 ± 1.9 | 0.228 ± 0.003 |
| MPC3 | 91.7 ± 0.2 | 0.227 ± 0.002 |
| MPC4 | 91.9 ± 1.1 | 0.228 ± 0.002 |
| MPC5 | 93.2 ± 1.0 | 0.229 ± 0.001 |

Milk protein-CLA microcapsules will oxidize during storage. Specifically, when the microencapsulated CLA comes into contact with the air in the microcapsules and the air in the powders, the unsaturated fatty acid chains will interact with oxygen. The primary oxidation product, hydroperoxide, is formed first, and an increase in the peroxide value (POV) can be observed at the time. After a period of time, the hydroperoxide is further decomposed and transformed into aldehydes, ketones, acids and other volatile secondary oxidation products that cause abnormal flavor of a product. As a polyunsaturated fatty acid of the $\omega$-6 series, CLA has a high content of hexanal in its secondary oxidation products, so the content of hexanal is often used to indicate the degree of secondary oxidation of CLA. Observed from the POV (FIG. 7A and FIG. 7B), after 45 days of storage at 35° C., the POV of CLA in the WPI+SC group increased first, then decreased, and then increased with the increase of storage time; and the POV was the highest on day 14, which was 27 meq/kg. The POV of CLA in the WPC group did not change much during the entire storage process, and was always within 20 meq/kg. In the MPC group, the POV of CLA increased first and then decreased, reached 146.1±9.0 meq/kg on the $7^{th}$ day and stabilized at about 80 meq/kg after 30 days. The oxidation stability of CLA was improved by the microcapsules prepared from the treated MPC. When the decalcification rates were 14.0% and 28.0%, the initial POVs of CLA in the corresponding microcapsules were 18.2±3.5 meq/kg and 16.0±3.4 meq/kg respectively, which were lower than the initial POVs of the MPC group. However, the oxidation rate of CLA in these two groups was faster in the storage process, and the POVs after 7 days were as high as 102.0±1.7 meq/kg and 92.2±0.9 meq/kg, which were higher than those of the MPC group. After 30 days, the POV dropped to 50.9±4.0 meq/kg and 28.9±1.5 meq/kg respectively. The POV of CLA in the group with the decalcification rate of 45.2% was always lower than the POV of the control group in the storage process. The POV of CLA in the group with a decalcification rate of 59.2% was always at a relatively low level (approximately 40 meq/kg) within 30 days of storage.

Due to the contingency of the measurement points, the highest point in a POV histogram is not necessarily the point with the largest POV during storage, so the POV can only preliminarily reflect the oxidation of the microencapsulated CLA. Therefore, the hexanal content of CLA in the microcapsules during storage was also tested. Observed from the change of hexanal value (FIG. 8A and FIG. 8B), the initial hexanal contents of the WPC and WPI+SC groups were 9.9±0.1 mg/kg and 13.3±0.1 mg/kg respectively. With the increase of storage time, the hexanal contents of the WPC and WPI+SC groups increased to 25.1±0.7 mg/kg and 57.7±0.4 mg/kg respectively at the $30^{th}$ day of storage. The hexanal content of the MPC group on the $45^{th}$ day was 295.4±20.4 mg/kg, which was much higher than the hexanal content of CLA in the WPC and WPI+SC groups. The oxidation stability of CLA was improved by the microcapsules prepared from the treated MPC. The hexanal content of the groups with the decalcification rates of 14.0% and 28.0% was generally higher than that of the group with the decalcification rate of 0%, and increased first and then decreased with the increase of storage time. This may be due to further decomposition of hexanal at the late storage period, or may be due to volatilization of the hexanal from the microcapsules into the air in the storage process, which was not collected during the sampling process. The hexanal content of the groups with the decalcification rates of 45.2% and 59.2% has been increasing with time. In general, during most of the storage time, the hexanal mass contained in the CLA microcapsules prepared from the MPC with different decalcification rates is ranked as follows: 28.0% group>14.0% group>0% group>45.2% group>59.2% group.

Figure 9A:
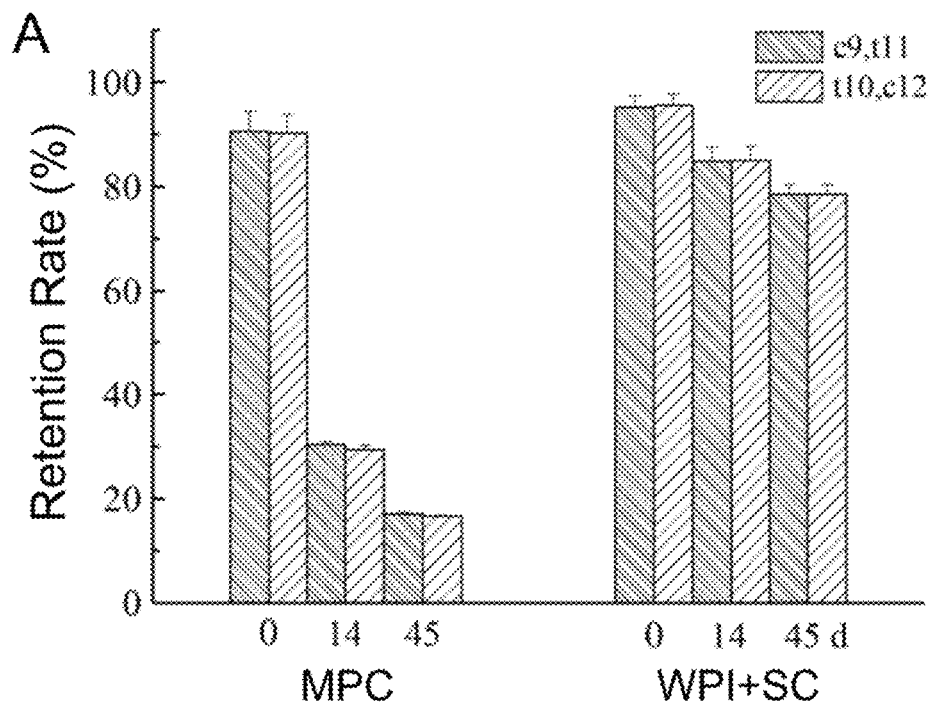
FIG. 9A Changes of CLA(MPC,WPI+SC) retention rate in microcapsule powder during storage.
Figure 9B:
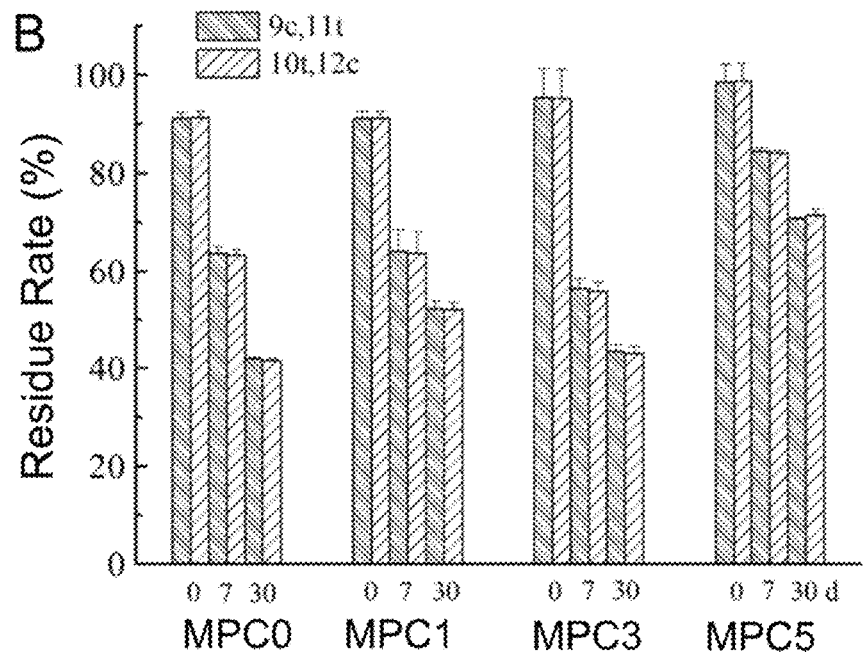
FIG. 9B Changes of CLA (MPC0, MPC1, MPC3, MPC5) retention rate in microcapsule powder during storage.

The POV and the hexanal content can only indirectly reflect the degree of oxidation of CLA, and cannot intuitively indicate the change of the CLA content in the microcapsule powder in the storage process. In order to further clarify the influence of micellar structure on the oxidation stability of milk protein-CLA microcapsules, in the storage process, the content of two main CLA isomers (c9,t11 and t10,c12) in the MPC and WPI+SC groups were tested at selected points (days 0, 14, and 45). After comparing the isomer content with that in fresh purchased CLA, the isomer content is expressed in terms of retention rate (%) (FIG. 9A and FIG. 9B). The results showed that the oxidation rates of the two main CLA isomers, c9,t11 and t10,c12, were the same. The change in CLA content in the MPC group containing the micellar structure was quite different from that in the WPI+SC group not containing the micellar structure. On day 0, the retention rate of CLA in the microcapsules of the MPC group was 90.5%, but the retention rate of CLA in the WPI+SC group was 95.2%. After storage at 35° C. for 30 days, the retention rate of CLA in the MPC group dropped to 42.0%, while the retention rate of CLA in the WPI+SC group was still as high as 78.5±1.5% after storage for 45 days. The improvement of the retention rate of CLA by the microcapsules prepared from the treated MPC has also been confirmed. The retention rates of CLA on day 0 in the groups with decalcification rates of 14.0%, 28.0% and 59.2% were 91.1%, 95.3% and 98.6% respectively. The overall trend is that the higher the decalcification rate, the higher the retention rate of CLA in the fresh microcapsule samples, which may be related to the formation speed of microcapsule shell layers in the spray-drying process. The higher the degree of decalcification, the smaller the number of casein micelles with stronger hydratability in the MPC solution of the corresponding wall material, the faster the water evaporation and the formation of the microcapsule shell layer in the spray-drying process, and the denser the shell layer. Therefore, the contact time between the CLA inside atomized droplets and dry air with higher temperature is shorter, and the loss of CLA is less. The retention rates of CLA in the microcapsules of groups with the decalcification rates of 14.0%, 28.0% and 59.2% decreased to 64.0%, 56.5% and 84.4% respectively after storage for 7 days. The retention rates of CLA after storage for 30 days were 52.3%, 43.4% and 70.7% respectively.

It can be seen that in the storage process, the oxidation rate and degree of CLA in the MPC group microcapsules having the micellar structure are higher than those in the WPI+SC group without micellar structure. That is, the casein micelle structure affects the protective effect of MPC on the core material. Therefore, compared with traditional milk protein ingredients, if MPC is to be used as a market-competitive microencapsulation wall material, both the structure and performance of the MPC need to be further improved. After proper processing and treatment, the application characteristics of MPC as a microencapsulation wall material can be effectively improved, and the microencapsulation efficiency and protection of the physical and chemical stability of the core material are improved.

What is claimed is:

1. A microcapsule, comprising:
    a wall material, and
    a core material,
    wherein the wall material comprises a pretreated milk protein concentrate (MPC),
    wherein the core material comprises one or more of vitamins, unsaturated fatty acids, probiotics, vaccines, and essential oils; and
    wherein the pretreated MPC is prepared by subjecting the MPC to any one or more of the following:
    a) stirring ion exchange resin with the MPC,
    b) adding an acid to the MPC, wherein the acid is selected from one or more of hydrochloric acid, sulfuric acid, acetic acid, and glucolactone, and then subjecting the MPC to ultrafiltration, and
    c) adding a calcium ion chelator to the MPC, wherein the chelator is selected from one or more of ethylene diamine tetraacetic acid (EDTA), citric acid, malic acid, and tartrate.

2. The microcapsule of claim 1, wherein a mass ratio of the ion exchange resin to the MPC in dry weight is 1:30 to 3:1.

3. The microcapsule of claim 1, wherein stirring the ion exchange resin with the MPC is performed and comprises:
    adding 0.1 g to 30 g of the ion exchange resin to 100 g of the MPC to obtain a mixed solution, and
    stirring the mixed solution for a period of time for treatment.

4. The microcapsule of claim 1, wherein the pretreatment is performed until a decalcification rate is 45% or above.

5. The microcapsule of claim 1, wherein when the ion exchange resin is used, a mass ratio of the ion exchange resin to the MPC in dry weight is 1:30 to 3:1; and wherein the pretreatment is performed until a decalcification rate is 45% or above.

6. The microcapsule of claim 1, wherein preparing the microcapsule comprises:
    homogenizing the pretreated MPC at 10 Mpa to 50 MPa,
    adding the core material according to a mass ratio of the core material to the wall material of 1:50 to 1:1 (w/w);
    stirring,
    dispersing by a high-speed shearing disperser; and
    homogenizing the mixture 2 to 6 times at a pressure of 10 MPa to 50 MPa to obtain a uniform emulsion.

7. The microcapsule of claim 6, wherein wherein preparing the microcapsule further comprises:
    spray-drying or freeze-drying the uniform emulsion to prepare microcapsule powder;
    wherein the spray-drying is performed at an inlet temperature of 120° C. to 160° C. and an outlet temperature controlled at 60° C. to 90° C.; and
    wherein the freeze-drying is performed by freezing the emulsion into a solid state under liquid nitrogen or at −80° C.

8. The microcapsule of claim 1, wherein an encapsulation rate of the core material is from about 84.4% to about 96.3%.

9. The microcapsule of claim 1, wherein the core material is an unsaturated fatty acid.

10. The microcapsule of claim 6, wherein the microcapsule emulsion forms a continuous viscoelastic interface.

* * * * *